United States Patent [19]

Schwartz

[11] Patent Number: 5,478,952
[45] Date of Patent: Dec. 26, 1995

[54] RU,RE/CARBON CATALYST FOR HYDROGENATION IN AQUEOUS SOLUTION

[75] Inventor: Jo-Ann T. Schwartz, Chadds Ford, Pa.

[73] Assignee: E. I. Du Pont de Nemours and Company, Wilmington, Del.

[21] Appl. No.: 398,638

[22] Filed: Mar. 3, 1995

[51] Int. Cl.⁶ .................. C07D 307/06; C07D 307/28
[52] U.S. Cl. ................ 549/325; 549/326; 568/885
[58] Field of Search ..................... 549/325, 326; 568/885

[56] References Cited

U.S. PATENT DOCUMENTS

| | | | |
|---|---|---|---|
| 4,550,185 | 10/1985 | Mabry et al. | 549/508 |
| 4,609,636 | 9/1986 | Mabry et al. | 502/183 |
| 4,659,686 | 4/1987 | Griffiths et al. | 502/183 |
| 4,985,572 | 1/1991 | Kitson et al. | 549/326 |
| 5,149,680 | 9/1992 | Kitson et al. | 502/185 |

FOREIGN PATENT DOCUMENTS

| | | |
|---|---|---|
| 6-157490 | 6/1994 | Japan. |
| 6-157491 | 6/1994 | Japan. |
| 6-179667 | 6/1994 | Japan. |

*Primary Examiner*—C. Warren Ivy
*Assistant Examiner*—Amelia Owens

[57] ABSTRACT

Improved hydrogenation catalysts consisting essentially of highly dispersed, reduced ruthenium and rhenium on carbon support and methods of making and using the same. Such catalysts exhibit high conversion rates in aqueous solution hydrogenation of hydrogenatable precursors (e.g., maleic acid, succinic acid, γ-butyrolactone, etc.) to tetrahydrofuran, 1,4-butanediol and mixtures thereof.

7 Claims, No Drawings

RU,RE/CARBON CATALYST FOR HYDROGENATION IN AQUEOUS SOLUTION

BACKGROUND OF THE INVENTION

1. Field of the Invention

This invention relates to an improved catalyst and method for using the catalyst for hydrogenation in aqueous solution. More specifically but not by way of limitation, the invention relates to the production of tetrahydrofuran, γ-butyrolactone, 1,4 butanediol and the like from a hydrogenatable precursor such as maleic acid, succinic acid or the like in aqueous solution in the presence of hydrogen and a catalyst consisting essentially of highly dispersed, reduced ruthenium and rhenium on a carbon support.

2. Description of the Related Art

Various methods and reaction systems have been proposed in the past for manufacturing tetrahydrofuran, γ-butyrolactone and 1,4-butanediol by catalytic hydrogenation of maleic acid, maleic anhydride, succinic acid and/or related hydrogenatable precursors. Also, a variety of hydrogenation catalyst have been historically proposed for this purpose including various transition metals and combinations of transition metals deposited on various inert supports, all as generally known in the art. For example, U.S. Pat. Nos. 4,985,572 and 5,149,680 disclose and claim a process for hydrogenating a carboxylic acid or an anhydride thereof to corresponding alcohol and/or carboxylic acid ester using a catalyst composition comprising an alloy of a noble metal of Group VIII and one other metal. In a comparative test a ruthenium and rhenium supported on graphitized carbon is used as a catalyst in a plug flow single pass hydrogenation of acetic acid. Also, Japanese patent application publications (Kokai) 6-157490, 6-179667 and 6-157491 disclose methods of preparing tetrahydrofuran by catalytic hydrogenation of maleic anhydride or maleic acid under milder conditions in the presence of an acidic substance using as catalyst a rhenium compound and a Group VIII metal in the first two references and a ruthenium compound in the latter. Comparative examples in the first two references illustrated the use of a ruthenium and rhenium on carbon catalyst without the acidic substance being present. However as a general rule these proposed catalytic reactions are predominantly conducted in an organic solvent or organic reaction media and not in an aqueous solution phase. In fact, at least one prior publication suggests that water and succinic acid may be considered as inhibitors to the desired catalysis, see Bulletin of Japan Petroleum Institute, Volume 12, pages 89 to 96 (1970). One notable exception to the lack of aqueous phase catalytic hydrogenation is the use of a carbon supported catalyst comprising 0.5% to 10% palladium and about 1% to 10% rhenium by total weight of supported catalyst in an aqueous solution hydrogenation reaction wherein the palladium is present on the carbon support in the form of crystallites having an average size of about 10 nm to 25 nm and the rhenium is present in a highly dispersed phase having an average size less than about 2.5 nm as described in U.S. Pat. Nos. 4,550,185; 4,609,636; and 4,659,686. Also, in a recently laid-open Japanese Kokai, Sep. 24, 1993, the use of reduced ruthenium and tin on an activated carbon support is disclosed in aqueous phase catalytic hydrogenation. This reference teaches the use of any Group VIII noble metal including palladium and ruthenium in combination with either tin, rhenium or germanium. The reference distinguishes the claimed subject matter from the previous Pd, Re/Carbon aqueous phase hydrogenation system of the prior art by virtue of specifically claiming the use of a carrier of porous carbon having a BET surface area of at least 2,000 $m^2/g$; a concept and limitation that is not characteristic of the Pd, Re/Carbon system of the U.S. Pat. Nos. 4,550,185 and 4,609,636 patents nor is this limitation of any critical significance relative to the present invention.

SUMMARY OF THE INVENTION

In view of the prior art and specifically the limited options associated with aqueous phase catalytic hydrogenation, the present invention provides a highly active and robust hydrogenation catalyst system that exhibits high performance during hydrogenation of a hydrogenatable precursor in an aqueous solution. More specifically, the invention provides a ruthenium and rhenium on carbon support catalyst wherein both reduced components exhibit a very high degree of dispersion and consistent compositional ratio when quantitatively analyzed at a spatial resolution on the order of a square nanometer; i.e., any microstructural differences are on the nanometer or sub-nanometer scale. This apparent atomic or near atomic scale dispersion of the reduced metals results in hydrogenation rates heretofore unattained by other known aqueous phase hydrogenation catalyst systems. The reduced ruthenium and rhenium on carbon support catalyst according to the present invention also exhibits improved longevity sustaining unexpectedly high hydrogenation rates over greater duration with more favorable loss of catalytic activity as a function of time.

Thus the present invention provides an improved hydrogenation catalyst consisting essentially of at least 0.1% by weight ruthenium and at least 0.1% by weight rhenium supported on carbon, said percentages based on total weight of supported catalyst, wherein both ruthenium and rhenium are present in a highly dispersed reduced stale; said carbon support is characterized by a BET surface area of less than 2,000 $m^2/g$ and said catalyst is characterized by a space-time-yield (STY) for conversion of maleic acid to tetrahydrofuran in excess of 600 grams of product per kilogram of catalyst per hour at 250° C. and 2,000 psig total pressure.

The present invention further provides an improved method for catalytic hydrogenation of a hydrogenatable precursor in an aqueous solution comprising the steps of:

(a) hydrogenating a hydrogenatable precursor in an aqueous solution in the presence of hydrogen and a catalyst, said catalyst consisting essentially of at least 0.1% by weight ruthenium and at least 0.1% by weight rhenium supported on carbon, said percentages based on total weight of supported catalyst, wherein both ruthenium and rhenium are present in a highly dispersed reduced state; said carbon support is characterized by a BET surface area of less than 2,000 $m^2/g$ and said catalyst is characterized by a space-time-yield for conversion of maleic acid to tetrahydrofuran in excess of 600 grams of product per kilogram of catalyst per hour at 250° C. and 2,000 psig total pressure; and then (b) recovering at least one hydrogenated product.

It is a primary object of the present invention to provide a catalyst system that involves reduced, highly dispersed states for both ruthenium and rhenium while supported on a porous carbon which is capable of sustaining in an aqueous solution the hydrogenation of a hydrogenatable precursor at space-time-yields in excess of 600 g/kg·hr. It is a further object of the present invention to provide a reduced ruthenium and rhenium supported on a porous carbon catalyst system that exhibits high dispersion as well as an essentially constant compositional ratio of ruthenium to rhenium when analyzed at a spatial resolution on the order of a nanometer across the catalyst particle and from particle to particle indicative of microstructural homogeneity at the nanometer or sub-nanometer level. Fulfillment of these objects and the presence and fulfillment of additional objects will be apparent upon complete reading of this specification and attached claims.

DESCRIPTION OF THE PREFERRED EMBODIMENTS

The hydrogenation catalyst according to the present invention involves both ruthenium and rhenium being present on a porous carbon support in a reduced, highly dispersed state. The catalyst comprises at least 0.1% by weight of each metal based on the total weight of the catalyst to insure at least reasonable catalyst activity. Preferably the metal loading on the carbon support will be from 0.5% to 10.0% ruthenium and 1.0% to 20.0% rhenium. A preferred catalyst for hydrogenation of maleic acid to THF contains about 1.0% ruthenium and about 4.0% rhenium.

The carbon support useful in the present invention can be generally any such material as commonly known and commercially available for use in this art. Preferably the carbon catalyst support is a porous particulate solid characterized by a size distribution typically ranging from 5 to 100 microns and a BET surface area typically ranging from a few 100 to nearly 2,000 $m^2/g$. Preferably the carbon support will be commercially available material having an average particle size of the order of 20 microns and a BET surface area from about 900 to about 1,500 $m^2/g$. The catalyst support can be manufactured such as to have a latent acid, neutral or basic pH. Optionally, the catalyst support can be treated prior to metal deposition by one or more techniques as generally known in the art such as impregnation with alkali metal salts and/or calcination.

Three distinct methods of preparing the highly dispersed, reduced ruthenium and rhenium on carbon support will be exemplified later. Each of these methods produces a hydrogenation catalyst of extraordinary space-time-yields when employed to hydrogenate maleic acid in an aqueous solution again as more fully explained and exemplified later.

One such method is to prepare a water solution of a soluble ruthenium compound and a soluble rhenium compound and then add this solution to the carbon support. The water is evaporated thus depositing the ruthenium and the rhenium compounds on the carbon support. The actual method of adding the solution to the support can be by any technique generally known to the art including by way of example but not by way of limitation; immersion, spraying, or the like. The dry or partially dried composite material is then subjected to a reducing atmosphere at elevated temperatures for a time sufficient to reduce both the ruthenium and the rhenium. The dry or partially dried catalyst can then be added to the reaction zone for use as a hydrogenation catalyst.

A second related method to the above is to perform the process entirely in the presence of water or the aqueous solution of the hydrogenatable precursor. In this technique the water solutions of the ruthenium compound and the rhenium compound are commingled with the solid carbon particle phase while chemical reduction is performed. The resulting catalyst exhibits the ability to sustain hydrogenation of maleic acid in an aqueous solution at STY values in excess of 600 g/kg·hr at 250° C. at 2,000 psig total pressure. This methodology is of particular value and commercial interest in that the co-depositing and co-reduction step can be literally performed in situ in the hydrogenation reactor and can be accomplished in the presence of reactants such as succinic and/or maleic acids. Also, both co-depositing and co-reduction techniques serve to further distinguish the ruthenium, rhenium on carbon catalyst from the prior teaching of palladium, rhenium on carbon in that sequential depositing and reduction of palladium and rhenium is required to produce good hydrogenation catalyst activity. The mere fact that in the instant case these co-deposited/co-reduced techniques produce the most uniform microstructure (as referenced and explained later in describing the meaning of nanometer or sub-nanometer microstructure) further supports a conclusion that observed unexpectedly high catalyst activity of the Ru, Re/C catalyst (i.e., peak STY≈1,200 and sustained STY>600) relative to the prior art activity of the Pd, Re/C catalyst (i.e., STY typically from 300 to less than 500) with its known non-uniformity and heterogeneity of crystallite distribution and microstructure is somehow interrelated on a cause and effect or at least a distinguishing characterization level. In other words, there is a fundamental difference in the microstructure of the instant catalyst system relative to the previously known aqueous hydrogenation catalyst system based on palladium and rhenium as well as an unexpected increase in catalyst activity.

The third method of producing the catalyst is to sequentially deposit and reduce the ruthenium on the carbon support and then add the rhenium compound such as to deposit and reduce the rhenium on the same carbon support. In this manner the pre-reduction of the ruthenium occurs before the depositing and subsequent reduction of rhenium. Again as in the above co-depositing and co-reduction methods, the intermediate ruthenium on carbon can be achieved either in aqueous solution or in the dry state. Also, this method affords the opportunity to perform the final depositing and reduction of the rhenium compound in situ in the hydrogenation reactor by adding the ruthenium on carbon along with perrhenic acid or the like directly to the hydrogenation reactor.

It should be further appreciated that various other methods or alternate modes of depositing the ruthenium and/or rhenium compounds on the carbon support, such as by selective precipitation or the like optionally with or without solvent washing to selectively remove less desirable companion anions all as generally known in the art, are contemplated as being equivalent methodologies for use in preparing the catalyst according to the present invention.

The ruthenium compounds useful in the present invention for preparing the catalyst can be generally any such compound that is either water soluble or can be readily converted to a water soluble or partially water soluble compound that can then be deposited on the carbon support. This would include by way of example but not by way of limitation such compounds as $RuCl_3 \cdot xH_2O$, $Ru(NO)(NO_3)_3$ and the like. Preferably ruthenium trichloride is used.

The rhenium compounds useful in the present invention for preparing the catalyst can be generally any such compound that is either water soluble or readily converted to a water soluble or partially water soluble rhenium compound by the action of an oxidizing acid solution, hydrogen peroxide, or the like. As such, the perrhenate aqueous chemistry including the corresponding rhenium oxide deposition is particularly useful. Preferably a perrhenic acid solution is employed.

The reducing agent employed to chemically reduce the ruthenium and/or rhenium can generally be any such reductant or reducing environment consistent with either liquid phase reduction or vapor phase reduction including by way of example but not by way of limitation; formaldehyde, hydrazine hydrate, hydroxylamine, sodium hypophosphite, sodium formate, glucose, acetaldehyde, sodium borohydride, hydrogen and the like. When a vapor phase reduction is employed involving gaseous hydrogen with or without an inert diluent gas such as nitrogen or the like in the presence of the solid catalyst precursor, typically the vapor phase reduction is performed at a temperature range of 100° to 500° C. (preferably 250°–300° C.) at atmospheric pressure.

The method of using the highly dispersed, reduced ruthenium and rhenium on carbon catalyst to hydrogenate a hydrogenatable precursor according to the present invention can be performed by various modes of operation as generally known in the art. Thus the overall hydrogenation process can be by use of a fixed bed reactor, various types of agitated slurry reactors, or the like operated in either a batch or continuous mode, wherein an aqueous liquid phase containing the hydrogenatable precursor is in contact with a gaseous phase containing hydrogen at elevated pressure and the particulate solid catalyst. Typically such hydrogenation reactions are performed at temperatures from about 100° C. to about 300° C. in sealed reactors maintained at pressures from about 1,000 to about 3,000 psig.

For purposes of the present invention a hydrogenatable precursor can be, in the broadest sense, any compound or material that can be chemically reduced by hydrogenation or hydrogen up-take. This would include, in particular but again not by limitation, various organic compounds containing unsaturation or oxygenated organic functional groups or both. Most particularly, the aqueous phase catalytic hydrogenation of maleic acid to γ-butyrolactone and tetrahydrofuran is illustrative of the utility of the method according to the present invention. In this regard and as illustrated in the examples, it should be appreciated that various products of the sequential hydrogenation reaction are also potential hydrogenatable precursors. In other words, in the conversion of maleic acid to tetrahydrofuran, the chemical reduction is known to be sequential involving the rapid addition of hydrogen across the double bond thus converting maleic to succinic acid followed by the slower addition of hydrogen forming potential intermediates such as γ-butyrolactone and/or butanediol and ultimately the desired tetrahydrofuran (corresponding to the up-take of five moles of $H_2$ and production of three mole of $H_2O$ per mole of THF). In commercial production the overall selectivity to THF production can be significantly influenced by optimizing reaction conditions including maintaining adequate acidity thus favoring ring closure and cyclic ether production at the expense of diol production, continuous vapor removal of the more volatile products, and subsequent separation and recycle of the lactone. Clearly in this case the γ-butyrolactone can be viewed as either a co-product or as a recycled hydrogenatable precursor reactant.

For purposes of the present invention when referring to reduced phases being highly dispersed with an essentially constant composition ratio of ruthenium to rhenium when analyzed at a spatial sensitivity on the order of a square nanometer, reference, is being made to the quantitative analysis of the respective elements ruthenium and rhenium observed or measured on a region of the catalyst support down to a physical dimension on the order of a nanometer. Literally this statement is describing a level of homogeneity that exists at relatively small physical dimensions that is consistent with the previous description that any microstructural differences associated with the reduced metals are on the nanometer or sub-nanometer scale. Again, this is consistent with the view that the catalyst of the instant invention involves the respective metals present on the catalyst support as an apparent atomic or near atomic scale dispersion. However it should be further appreciated that such description, observations and measurements do not exclude the presence of additional microstructure at dimensions larger than the nanometer limit, nor observable changes in the microstructure at slightly above the nanometer level associated with the choice of methods of preparation and with aging of the catalyst during use as well as undetectable labile structural features below the nanometer observation limit (all of which are presently felt to be to some degree characteristic of the instant catalyst system).

For example and in reverse order, it is generally known that preparation of bimetallic catalyst containing rhenium (rhenate to rhenium heptaoxide deposition) implicitly involves mobility (see S. B. Ziemecki. G. A. Jones and J. B. Michel, "Surface Mobility of $Re_2O_7$ in the System $Re^{7+}Pd^0$/γ-$Al_2O_3$", Journal of Catalysis 99, pp. 207–216, 1986), thus suggesting at least the possibility of migration of the rhenium below the imageable limitation. With respect to aging of the catalyst during use an imageable ruthenium phase has been observed in used catalyst where initially no imageable ruthenium or rhenium were present suggesting some form of mobility associated with the ruthenium. However, the development of imageable ruthenium during use is generally of the order of the average pore size of the porous carbon support (i.e., typically 20 Å or the like) which is still a more highly dispersed state than that previously associated with prior art catalyst systems such as palladium and rhenium on carbon. Also, an imageable ruthenium may be observed depending on the method of preparation of the catalyst. Thus a catalyst made by sequential deposition and reduction involving ruthenium being deposited and reduced prior to deposition and reduction of rhenium may exhibit some imageable ruthenium microstructure at a few nanometers or slightly larger size. The deposition and reduction of ruthenium in the absence of rhenium may produce detectable ruthenium ensembles not associated with the microporous structure of the carbon and not necessarily detrimental to the development of the desirable high activity catalyst felt to be associated with the highly dispersed state of the metals at constant composition ratio. Typically the co-deposited and subsequently co-reduced catalyst is remarkably free of any imageable phase or surface crystallite microstructure and as such is felt to be the preferred catalyst for purposes of the instant invention.

The following examples are presented to more fully demonstrate and further illustrate various individual aspects and features of the present invention while the comparative examples and showings are intended to further illustrate the differences and advantages of the present invention. As such the examples are felt to be non-limiting and are meant to illustrate the invention but are not meant to be unduly limiting in any way particularly with respect to ultimate properties of the improved catalyst and utility of the claimed improved process.

EXAMPLE 1

Aqueous solutions of $RuCl_3 \cdot xH_2O$ (2.0305 grams of 1% ruthenium solution) and $HReO_4$ (1.104 grams of 7.7% rhenium solution) were mixed and the resulting solution was added to 2.03 grams of particulate carbon support (average particle size about 20 μm) characterized as intrinsically acidic (pH=4–4.5) with a BET surface area of about 1,500

$m^2/g$. The mixture was dried over night at 110° C. at reduced pressure (in vacuo) with a nitrogen purge. The dried catalyst was then placed in 150 cc quartz boats in a 1500 cc, 2.5 inch diameter, quartz tube oriented horizontally in a tube furnace. A nitrogen purge was carded out at room temperature for 15 minutes at a flow of 500 cc/min. The flow was switched 100 cc/min of helium and held for 25 minutes. The temperature was then ramped to 150° C. for one hour. After the hour hold, 100 cc/min of hydrogen was added to the flow and this was held for one hour at 150° C. The temperature was then raised to 300° C. with 1:1 $H_2$—He flow and then held for eight hours. After this time period the flow was switched back to helium and the catalyst was cooled in helium overnight. Once the temperature was less than 50° C., the catalyst was passivated for 30 minutes in flowing 1% $O_2$ in $N_2$. The resulting 1 wt. % Ru and 4 wt. % Re on carbon catalyst was tested in the reactor as described in following examples. The catalyst when examined by conventional x-ray diffraction and high resolution transmission electron microscopy showed no imageable metal crystallite structure (i.e., no separate structures> 10 Å in size other than background carbon structure); yet, chemical analysis with EDX confirms the one to four weight ratio of ruthenium to rhenium is essentially uniformly present across the carbon particle and from particle to particle.

Thus it should be appreciated that for purposes of claiming the present invention the use of the phrase "wherein both said ruthenium and rhenium are dispersed with a constant compositional ratio of ruthenium to rhenium when analyzed by STEM across the catalyst particle at a spatial resolution on the order of a square nanometer" means as illustrated above. The measurement is made using a field emission STEM that involves a highly focused electron beam impinging on approximately one square nanometer of the catalyst surface (i.e., transmission through the catalyst of an electron beam with a cross sectional dimension of one nanometer square).

EXAMPLE 2

2.0216 Grams of a 1% ruthenium content aqueous ruthenium trichloride solution was added to 2.07 grams of a particulate carbon support having a BET surface area of 1,500 $m^2/g$ and characterized as intrinsically acidic (pH 4–4.5). The mixture was dried over night at 110° C. at reduced pressure (in vacuo) with a nitrogen purge. Reduction of the ruthenium metal salt deposited on the carbon support was then carded out on the dry material essentially as described in Example 1.

EXAMPLE 3

0.5100 Grams of a 1% ruthenium solution derived from $RuCl_3 \cdot xH_2O$ was mixed with 0.2780 grams of a $HReO_4$ solution (7.7% Re from $Re_2O_7$). To this was added 35.2574 grams of a 7% succinic acid solution. This solution was added to a 125 mL Hastalloy C autoclave along with 0.5035 grams of a particulate acidic carbon (BET 1,500 $m^2/g$). The reactor was checked for leaks with nitrogen and then hydrogen was charged to the reactor and the reaction was carded out as described in Examples 4–15.

EXAMPLES 4 through 15

In order to evaluate the ruthenium/rhenium on carbon catalysts prepared according to the present invention, a series of batch hydrogenation reactions were performed using succinic acid as the hydrogenatable precursor (i.e., reactant). The equipment employed was a 125 mL autoclave supplied by Autoclave Engineers of Erie, Pa. The autoclave was equipped with a magnetic coupled stirring device which was driven by an air motor. A set of removable baffles (three vertical strips of Hastalloy C welded to two Hastalloy C rings) were used to help agitation. Gases were pumped into the reactor using a Haskell pump capable of pumping at up to 2,500 psig. The hydrogen used was CP grade from a cylinder, the nitrogen was from a cylinder, the succinic acid was Baker Analyzed reagent grade crystal and the water was deionized water. Seven weight percent solutions of succinic acid were made in 500 gram batches by dissolving 35 grams of succinic acid in 465 grams of deionized water. The solutions were heated to 30° C. to completely dissolve the succinic acid. The solutions were then titrated to precisely determine the percent acid. The procedure employed involved adding the catalyst (typically about 0.1 to 0.5 grams) into the reactor followed by 35 grams of 7% succinic acid solution. The head was then placed on the reactor and bolted into place and torque down. Nitrogen was then pumped into the reactor using the Haskell pump to 2,400 psig to test for any leaks in the system. If pressure was not holding, leaks were detected with Snoop and fixed. When no leaks were detected, the nitrogen was slowly vented. After venting the nitrogen to atmospheric pressure, hydrogen was pumped into the reactor with the Haskell pump to 1,200 psig. The stirrer was set to 700 rpm and the heat was mined on. The contents in the reactor were heated to 250° C. which took about 1 hour to reach. When the temperature inside reached 250° C. the stirring was continued for 3 hours. After stirring at 250° for 3 hours the heater was turned off and cooling water was turned on to the jacket surrounding the reactor. When the contents of the reactor cooled to below 25° C. (about 0.5 hours) the air motor was mined off and the hydrogen was vented very slowly. When the hydrogen was vented to atmospheric pressure the bolts were removed. The contents were quickly removed from the reactor using a 60 mL disposable syringe with a large bore stainless sled needle. After the sample was removed from the reactor 10 mL were filtered using a 10 mL disposable syringe and a 0.45 micron PTFE syringe filter. A sample of this was analyzed by GC for tetrahydrofuran, 1-propanol, n-butanol, gammabutyrlactone and 1,4-butanediol using a Hewlett Packard 5890A instrument and a portion was titrated for remaining succinic acid. The titration involved about 8 grams of filtered solution weighed into a 150 mL beaker with recording of the weight to 4 decimal places. A magnetic stir bar and stirring plate was used to stir the solution. A couple of drops of phenothalein solution was added and splashed solution was rinsed from the sides with deionized water. The titration with 0.1N NaOH solution was conducted to a pink (30 second) endpoint. The resulting data for various catalyst made according to the instant invention as well as several controls characteristic of previously known aqueous hydrogenation catalysts of palladium and rhenium on a carbon support are presented in the following Table.

TABLE

| Exp. | Catalyst | amt. | GBL | DBO | THF | PrOH | BuOH | % conv. |
|---|---|---|---|---|---|---|---|---|
|  | 1%Pd,4%Re | 0.50 g | 1.47** | 6.85** | 7.83** | 1.57** | 2.54** | 92 |
|  | carbon A | 0.25 g | 8.82 | 3.59 | 6.44 | 0.27 | 0.48 | 53 |
| 4 | 1%Ru,4%Re[(a)] | 0.25 g | 0.08 | 0.49 | 16.9 | 1.45 | 1.21 | 99 |
| 5 | carbon A | 0.10 g | 6.27 | 2.31 | 8.73 | 1.09 | 1.04 | 65 |
| 6 | 1%Ru,4%Re[(a)] | 0.25 g | 0.08 | 0.51 | 16.6 | 1.70 | 1.20 | 99 |
| 7 | carbon B | 0.10 g | 8.19 | 0.51 | 6.55 | 0.28 | 0.16 | 37 |
| 8 | 1%Ru/C + 4%Re[(b)] | 0.25 g | 0.29 | 0.88 | 14.8 | 2.51 | 1.80 | 98 |
| 9 | carbon A | 0.10 g | 10.5 | 0.37 | 3.76 | 0.46 | 0.52 | 25 |
| 10 | 1%Ru/C + 4%Re[(b)] | 0.25 g | 0.14 | 0637 | 15.7 | 2.16 | 1.59 | 98 |
| 11 | carbon B | 0.10 g | 10.2 | 1.45 | 5.58 | 0.68 | 0.71 | 41 |
| 12 | 1%Ru,4%Re[(c)] | 0.50 g | 1.03 | 0.74 | 16.2 | 0.96 | 1.21 | 92 |
| 13 | carbon A | 0.25 g | 4.02 | 0.88 | 11.8 | 1.42 | 1.8 | 78 |
| 14 | 1%Ru,4%Re[(c)] | 0.25 g | 1.02 | 0.87 | 15.23 | 1.53 | 1.53 | 94 |
| 15 | carbon B | 0.10 g | 10.19 | 0.75 | 5.56 | 0.57 | 0.77 | 38 |

**all data in mmoles, with THF reported including credit for vapor phase based on carbon mass balance calculation
[(a)]Ru and Re co-reduced in $H_2$: aqueous solution of $RuCl_3$ & $HReO_4$ deposited on carbon, dried overnight @ 110° C. in vacuo with $N_2$ purge, then co-reduced for 8 hrs. @ 300° C. in 1:1 mix $H_2$/He, per Example 1.
[(b)]Ru pre-reduced in $H_2$: 1% Ru as $RuCl_3$ solution deposited on carbon, dried overnight @ 110° C. in vacuo with $N_2$ purge, then reduced for 8 hrs. @ 300° C. in 1:1 mix $H_2$/He, and added to reactor with $HReO_4$ solution, per Example 2.
[(c)]Ru and Re co-reduced in reactor: aqueous solution of $RuCl_3$ & $HReO_4$ with 35 g of 7% succinic acid added to reactor with particulate carbon, purged with $N_2$ and then 1,200 psi $H_2$ @ 250° C., final pressure 2200–2300 psig for in-situ co-reduction, per Example 3.
Carbon A: particulate carbon having a BET surface are of ≈1,500 $m^2$/g and intrinsically acidic (pH = 4–4.5)
Carbon B: particulate carbon having a BET surface are of ≈1,000 $m^2$/g and intrinsically basic (pH = 8–9)

EXAMPLES 16

Continuous runs were carded out in a back-mixed slurry reactor by charging the catalyst prepared according to Example 1 in 150 mL of water into a 300 mL Hastelloy C autoclave equipped with an agitator, a thermocouple, feed lines for hydrogen and maleic acid, and an exit line through which the product was swept out with the excess hydrogen and water vapor. Preceding the reaction, the catalyst slurry was activated at 250° C. under a 1,000 mL/min hydrogen flow at 2,000 psig for one hour. Thereafter, maleic acid was fed as a 40% by weight aqueous solution at various feed rates and the reactor was maintained at 2,000 psig and 250° C. The volatile products and water were swept out of the reactor at a rate controlled by the hydrogen feed rate. The hydrogen feed rate was adjusted so that the amount of water carried out with the exiting hydrogen gas was balanced with the amount of water added with the maleic acid feed and the amount produced by the reaction. The reactor level was maintained constant at 100–200 cc. In all cases an excess of hydrogen was fed relative to the mount consumed by the reaction and the hydrogen feed rate was shown not to influence catalyst performance.

The maleic acid solution was fed at a low initial feed rate and was increased by 2–3 cc/hr about every 8 hours until the acid level in the reactor reached 8%. After this the maleic acid feed rate was adjusted as necessary to maintain the reactor acid level between 6–10%.

The runs were made without interruption for up to several weeks, and time intervals during steady state operation were selected for analysis, generally of 8 to 24 hours duration. The product composition data generated during steady state operation was averaged to give the average production rates (g/hr) of THF (tetrahydrofuran), BDO (1,4-butanediol), GBL (gammabutyrolactone), PrOH (n-propyl alcohol), BuOH (n-butyl alcohol), and alkanes (primarily butane and methane). The product composition was measured by condensing a portion of the volatilized products and water in the exit gas stream and collecting the liquid product. The volume of liquid product collected each hour was measured, and its composition analyzed using a calibrated gas chromtograph (GC) equipped with a flame ionization detector. The remaining uncondensed products (THF and alkanes) still in the exit gas stream were analyzed by measuring the gas flow rate and then analyzing the composition of the gas stream every two hours using GC procedures similar to those used for liquid analysis. The reactor contents were sampled every four hours and analyzed by GC and titration. Titration with sodium hydroxide was used to monitor the acid concentration in the reactor and the results are reported as percent by weight of succinic acid. The GC analysis was carded out using a Supelcowax 10 capillary column (30 m×0.052 mm) which was maintained at 75° C. for 5 minutes after injection and then heated at 10° C. per minute to a final temperature of 200° C. The combination of these three analyses permits calculation of the catalyst performance in terms of space-time-yield (STY) (calculated as grams of THF produced per kilogram of catalyst per hour), product selectivity and the mass balance for each run.

In the first run the catalyst used was 3.5 grams (dry weight) of a 1% ruthenium and 4% rhenium on a carbon support. The initial maleic acid feed rate was 6 cc/hr, and this was increased in 2 cc/hr increments up to 20 cc/hr, at which point the acid level in the reactor reached 8%. After this the feed rate was adjusted to maintain the acid level at 6–10%. The initial THF production rate (at the lowest maleic acid feed rate) was 200 STY (g THF/kg catalyst·hr). As the acid feed rate was increased the production rate continued to increase reaching as high as 1,200 STY by the time the feed rate reached 20 cc/hr. Over the next three weeks of operation the activity slowly declined, finally reaching a THF production rate of about 600 STY.

A second comparative run was made as in the above run, except the catalyst was replaced with 10 g of a 1% palladium and 4% rhenium of the same carbon support. The maleic acid feed was started at 12 cc/hr and was increased over five days to 28 cc/hr. Over this period the acid level in the reactor increased up to 5%, and the THF production rate increased up to a maximum of 495 STY.

It should be appreciated that for purposes of claiming the present invention the use of the phrase "said catalyst is characterized by a space-time-yield for conversion of maleic acid to tetrahydrofuran in excess of 600 grams of product per kilogram of catalyst per hour at 250° C. and 2,000 psig total pressure" means a catalyst that performs essentially as illustrated in Example 16. In other words, the phrase refers to characterizing the highly active and robust hydrogenation catalyst system according to the instant invention in terms of the catalysts ability to sustain the production of THF in a continuous mode of operation wherein the volatile product is swept from the reactor by the excess gaseous phase containing the reactant hydrogen all at the specified conditions (i.e., 250° C. and 2,000 psig total pressure). But even more importantly, the characterization reaction is conducted such as to afford the catalyst the opportunity to exhibit full reaction potential and not be subject to stoichiometric limitations of either reactant (i.e., the hydrogen or the hydrogenatable precursor). As a pragmatic consideration and as illustrated in the example, the rate of flow of reactants to the reactor are adjusted (increased) until the catalyst is being utilized to its fullest extent. Typically this is achieved by monitoring the residual acid content of the reactor and increasing the reactant flow until at least about a 5% acid or higher steady state is present in the reactor. At acid concentrations below this value the STY will not be optimized and the tendency to over hydrogenate the product will also reduce the selectivity to THF. Experience indicates that operating at or above this residual acid level produces STY values heretofore unachieved by prior art catalyst systems. Residual reactor acid levels as high as twenty percent have been successfully achieved but as a pragmatic consideration succinic acid solutions of this concentration will solidify unless maintained at high temperature.

The advantages and benefits of the present invention are felt to be significant and numerous. First and foremost, the catalyst system of the instant invention affords and provides a method for sustaining catalytic hydrogenation of maleic acid dissolved in water at space-time-yields heretofore unachievable. Furthermore this aqueous phase hydrogenation is achieved without the use of external additives or agents such as the presence of strong acid nor does the hydrogenation depend on the use of extremely high BET surface area carbon support. Consequently, the instant catalyst and method of use is amenable to a continuous mode of commercial operation involving the addition of maleic acid to the catalytic reactor as an aqueous solution and the continuous recovery of gaseous product by sweeping the other reactant, hydrogen, through the reaction zone, all of which represent and translate into a significant economic advantage particularly at the commercial scale associated with contemporary THF production. Further cost savings are realized by virtue of the inherent lower cost of the respective metals of the catalyst and the lower capital investment per unit production associated with the high STY of the catalyst. Also the discovery of the high dispersion at the nanometer or sub-nanometer scale affords a method of characterizing the catalyst and its respective performance which in turn has pragmatic value for operating a commercial scale plant.

Having thus descried and exemplified the invention with a certain degree of particularity, it should be appreciated that the following claims are not to be so limited but are to be afforded a scope commensurate with the wording of each element of the claim and equivalents thereof.

I claim:

1. A method for catalytic hydrogenation of a hydrogenatable precursor in an aqueous solution comprising the steps of:

(a) hydrogenating a hydrogenatable precursor in an aqueous solution in the presence of hydrogen and a catalyst, said catalyst consisting essentially of at least 0.1% by weight ruthenium and at least 0.1% by weight rhenium supported on carbon, said percentages based on total weight of supported catalyst, wherein both ruthenium and rhenium are present in a highly dispersed reduced state; said carbon support is characterized by a BET surface area of less than 2,000 $m^2/g$ and said catalyst is characterized by a space-time-yield for conversion of maleic acid to tetrahydrofuran in excess of 600 grams of product per kilogram of catalyst per hour at 250° C. and 2,000 psig total pressure; and then (b) recovering at least one hydrogenated product.

2. A method according to claim 1 wherein the hydrogenatable precursor is selected from the group consisting of maleic acid, maleic anhydride, fumaric acid, succinic acid, maleic acid, the esters corresponding to these acids, γ-butyrolactone and mixtures thereof.

3. A method according to claim 1 wherein both said ruthenium and rhenium are dispersed at the nanometer or sub-nanometer scale.

4. A method according to claim 1 wherein both said ruthenium and rhenium are highly dispersed with a constant compositional ratio of ruthenium to rhenium when analyzed by STEM across the catalyst particle at a spatial resolution on the order of a square nanometer.

5. A method according to claim 1 wherein said catalyst is made by the method comprising, in sequence, the steps of: depositing both a ruthenium compound and a rhenium compound on a carbon support; drying the carbon support containing both said ruthenium compound and said rhenium compound; and then reducing the ruthenium and rhenium.

6. A method according to claim 1 wherein said catalyst is made by the method comprising, in sequence, the steps of: depositing both a ruthenium compound and a rhenium compound on a carbon support and then reducing the ruthenium and rhenium, in situ, in a hydrogenation reactor wherein said hydrogenating of said hydrogenatable precursor in an aqueous solution takes place.

7. A method according to claim 1 wherein said catalyst is made by the method comprising, in sequence, the steps of: depositing a ruthenium compound on a carbon support; drying the carbon support containing said ruthenium compound and then reducing the ruthenium before depositing and reducing a rhenium compound on said carbon support.

\* \* \* \* \*